United States Patent
Knapp et al.

(10) Patent No.: US 6,498,645 B1
(45) Date of Patent: Dec. 24, 2002

(54) INSPECTION OF LIQUID INJECTABLE PRODUCTS FOR CONTAMINATING PARTICLES

(76) Inventors: Julius Z. Knapp, 22 Foxwood Dr., Somerset, NJ (US) 08873; Gerald W Budd, 36853 Heatherton Rd., Farmington, MI (US) 48335

( * ) Notice: Subject to any disclaimer, the term of this patent is extended or adjusted under 35 U.S.C. 154(b) by 148 days.

(21) Appl. No.: 09/706,662

(22) Filed: Nov. 5, 2000

(51) Int. Cl.$^7$ ............................................... G01N 21/90
(52) U.S. Cl. .................................. 356/427; 250/223 B
(58) Field of Search ................................. 356/427, 426, 356/428, 237, 238, 240; 250/223 B (56) References Cited

U.S. PATENT DOCUMENTS

| | | | | |
|---|---|---|---|---|
| 4,676,650 A | * | 6/1987 | Bjorndal et al. | 348/127 |
| 5,365,343 A | * | 11/1994 | Knapp | 356/239.5 |
| 5,523,560 A | * | 6/1996 | Manique et al. | 209/526 |
| 5,694,221 A | * | 12/1997 | Knapp | 250/223 B |

* cited by examiner

Primary Examiner—Georgia Epps
Assistant Examiner—Richard Hanig (74) Attorney, Agent, or Firm—Israel Nissenbaum (57) ABSTRACT

A method for the substantially complete detection of all particles, within a predetermined size range, contained in an injectable solution comprising the steps of: a) pre-positioning particles in the container whereby rotation of the container causes substantially all of the particles in the injectable solution in the container to rotate in a shell volume adjacent the inner walls of the container, with said shell volume having a predetermined thickness; b) illuminating all the particles rotating within the shell volume with light; and c) detecting at least one of light scatter, light reflection and light extinction caused by said particles, with detectors having a depth of focus of detection in opposite volumes of the shell along a cross sectional diameter of the container perpendicular to the sensing array. Wherein the detectors are positioned, relative to the container whereby a focal point of detection which initially coincides with a focused plane through the vertical axis of the container, whereby the size of detected particles in the opposite volumes is accurately adjusted to an actual size by either calculation or by calculated offset of the focused planes; and wherein there are at least two directed lights, spaced 120° from each other, with said containers being masked relative to each of said lights whereby each light illuminates different opposite volumes of the shell, with each of said volumes being bounded by a 90° arc segment of the container, which is symmetrically disposed around the principal optical plane of the system.

13 Claims, 2 Drawing Sheets

INSPECTION OF LIQUID INJECTABLE PRODUCTS FOR CONTAMINATING PARTICLES

FIELD OF THE INVENTION

This invention relates to procedures and devices utilized in the visual or optical inspection of transparent containers for the presence of contaminating particulate matter and particularly to inspection of injectable pharmaceutical preparations.

BACKGROUND OF THE INVENTION

There is an ethical and legal obligation to ensure that pharmaceutical injectable solutions are free of 'visible' particle contaminants following manufacture and prior to their clinical use. This legal obligation can be satisfied by the use of a labor intensive and costly 100% manual inspection of injectable solutions. Less costly automated particle detection systems have been developed. However, in order to satisfy Good Manufacturing Practice, automated inspection systems must be validated prior to any pharmaceutical use. In the validation demonstration, the functioning of the automated system must be shown to be at least as effective in detecting and rejecting containers with 'visible' contaminating particles as the preceding manual inspection.

The performance of human 'visible' particle inspection has been characterized in published reports as a probabilistic process without a sharp particle size accept/reject decision threshold (i.e., a soft decisional process). In the production of an injectable product under good control, the distribution of contaminating particles is approximately hyperbolic, with the concentration of contaminating particles decreasing rapidly as particle size increases. The effect of the 'soft' accept/reject decision threshold is that a proportion of particle-contaminated containers that should be rejected are accepted. A false reject rate of good containers also results from the 'soft' accept/reject decision process. Due to the increased number of containers with particles well below both clinical and control interest, a disproportionate number of the containers that should be accepted are rejected. This disproportionate false reject rate imposes additional costs on the quality assurance program.

Validation of alternative equipment or methods is a Good Manufacturing Practice requirement. The validation of a contaminating particle inspection system is a demonstration that the automated inspection system rejects those containers identified in a manual inspection to be contaminated with "visible" particles. It must show that the rejection capability of the automated system is at least equal to or better than that achieved by the preceding human inspection method. This demonstration must be successfully completed prior to any production use of any proposed automated system.

This demonstration is based on an established statistically evaluated human 'visibility' performance benchmark. To make possible statistical comparisons and evaluations of particle contamination, an inspection model was defined with a statistically described rejection zone boundary. As currently accepted in the pharmaceutical field the Reject Zone includes the group of particle contaminated containers rejected in 70% of a series of manual container inspections. The group of containers with a manual rejection probability equal to or greater than 70% constitute the "must reject" visible particle contaminated group.

Holographic measurements found that the size of the contaminating particles that resulted in the 70% reject rate was 100 $\mu$m. This determination was made with the particle contaminated containers that were rejected in a 17 second, timed single container inspection performed under 225 foot-candles of illumination, the inspection time is equally divided against a black and white background. The holographic data was correlated with the statistically evaluated probability of detection data to define the minimum 'visible' particle size of 100 $\mu$m. Accordingly in present practice all containers with 100 $\mu$m or larger contaminating particles are considered to be 'must rejects'.

This Reject Zone definition has become a de-facto world standard in validation demonstrations and any proposed automated inspection device must function with at least the capability of the preceding manual inspection. This equivalent functionality is demonstrated by the achievement of an equal or higher rejection rate for the containers identified in the manual inspection to have 'must reject' contaminating particles that are 100 $\mu$m or greater.

When current commercially available automated inspection systems were evaluated according to this standard, it was determined that none could demonstrate, in a single inspection, results as secure or as selective as that achieved by human beings. The proportion of "must-reject" containers rejected in a single automated inspection is between half and two thirds that of a skilled human inspector.

As a result, in order to validate these automated inspection systems (to match their inspection security to that of the preceding manual inspection), a two inspection sequence is currently employed. only containers accepted in both inspections are accepted for stock. Containers rejected in either of the two sequential inspections are eliminated.

It has been determined that the limiting particle rejection/detection probability for an inspection system is the proportion of the liquid contents that have been examined for particulate contamination. A complicating factor is that the position of a contaminating particle in a container at the start of each inspection is completely random. This random initial particle position results in random distribution of particle orbits and velocities within the container. The random particle velocity distribution ranges from zero-to some design maximum.

A defined velocity of particle movement is employed to distinguish between contaminating particles and stationary container markings and optical defects. Particles that do not traverse the fractional inspected volume or that move with insufficient velocity are not detected. To improve the inspection security results, the two-inspection 'game of chance' technique to reduce the effect of the random particle position and velocity is employed. Application of classical probability theory shows that particle detection security is enhanced but the discrimination of the accept/reject decision compared to manual inspection is impaired when this inspection technique is employed. The cost for this improvement in detection probability is a four to six fold increase in the false rejection rate of the manual inspection.

Ideally, secure detection, sizing and identification of the contaminating particulates is an essential part of the control of the production of pharmaceutical injectable products. However, secure detection of randomly occurring and randomly positioned particles in sealed transparent containers requires inspection of the full volume of the container. In addition, accurate particle sizing in the present automated inspection systems requires sharp particle images. However, with present art, the sharp image requirement cannot be achieved for the size range of containers used for pharmaceutical injectable products.

In addition, only a portion of the contents of the container volume is normally inspected for contaminating particles and accordingly the security with which 'must reject' containers are rejected in the partial container volume inspection cannot exceed the proportion of the container volume containing contaminating particles inspected.

U.S. Pat. No. 3,627,423, issued Dec. 14, 1971, to one of the present inventors, discloses an improvement in particle contrast, and thus detectability, that results from the use of narrow aperture lighting of the liquid volume contents of the container. This patent teaches that narrow aperture lighting of the liquid volume contents of the container that transits the glass envelope or the container in a near perpendicular condition minimizes the reduction in particle contrast that occurs when a broad area light source is employed for the inspection. The use of narrow aperture lighting of the liquid volume contents of the container to produce forward scatter lighting also minimizes the reduction of particle signal dynamic range that occurs when glare reflections occur at the meniscus or the container bottom. Glare reflections are produced when a bottom mounted light source parallel to or on the container axis is employed for the inspection. The teachings of this patent are incorporated herein by reference thereto.

At present only one automated inspection method, U.S. Pat. No. 5,365,343 ('343 patent) issued Nov. 15, 1994, by one of the present inventors, can equal or surpass the two important attributes of the human inspection for contaminating particles in sealed containers (the teachings of this patent are also incorporated herein by reference thereto). These attributes are the reliability of detection of these contaminating 'visible' particles and the selectivity of the human accept/reject inspection characteristic. Both attributes are evaluated with statistical measures derived from the probabilistic analysis of human inspection results.

In the '343 patent, an imaging lens is used at its maximum energy collecting capability and its maximum resolution to achieve maximum particle detection depth. Two light sources are employed, a forward scatter light source is used for small and low contrast particle detection. A second collimated light source, with intensity at the detection plane ranging from 2 to 10%, is used as a back lighting means. The contaminating particles are sized numerically by the peak change, either positive or negative, in light flux collected from the moving particle. This patent teaches that the light flux collected from an image and its blur surround is essentially constant for a controlled displacement around the plane of best focus. This measurement approach avoids reliance on sharply defined image edges to detect and size particles, and it results in a total light flux particle measurement. It relies, however, on the presence of uniform illumination level for the inspected container and system measurement stability. This reliance results in particle detection variability determined by the variation in the realizable illumination uniformity of the inspected container and variation of the detection capability of the system.

The use of the described light flux sizing makes it possible to inspect the full volume of a container up to 30 mm in diameter with a 75 mm focal length lens at maximum aperture of f stop equal to 1.8. The previous detection volume limit was imposed by detection volumes 1 to 3 millimeters thick centered on the axis of the container and extending through its liquid contents. Since the reliability of detecting particles in a container is proportional to the total container volume inspected, inspection reliability for containers up to 30 mm in diameter approaches 100% with the use of the teachings of this patent. Determination of the size of a detected particle is achieved with a stored transfer curve of particle size versus the light flux peak detected. This methodology requires both light source and measurement system stability to maintain the calibrated particle sizing accuracy.. Particles are detected by the variation of light level received in each element of the photo detector. Any change in the stability of the light source or the measurement system affects the peak value of the detected light flux due to a particle and thus the particle sizing accuracy. This approach sacrifices particle image shapes to achieve secure detection of the particle signal throughout the volume of the container.

SUMMARY OF THE INVENTION

It is an object of the present invention to transform the present probabilistic detection of contaminating particles present in a container, even larger than 30 mm in diameter, into a deterministic detection and accurate measurement process.

It is a further object of the present invention to provide a method that evaluates the blurred image of light flux based particle measurement with a direct, physically based particle size evaluation in a defined area.

It is a still further object of the present invention to provide a method that transforms the present random array of particles within a container into a positioned array in a defined portion of the container which can be inspected with higher accuracy.

It is yet another object of the present invention to provide a means for accurate measurement of the blur fringe images of particles within all volumes of the defined portion of the container having the pre-positioned particles.

Generally the present invention comprises a method for the substantially complete detection of all particles, within a predetermined size range, contained in an injectable solution, in a transparent container. In preferred embodiments the container has a circular cross section, though some containers may depart from circular symmetry in less preferred embodiments. The method comprises the steps of:

a) pre-positioning particles in the container whereby rotation of the container causes substantially all of the particles in the injectable solution in the container to rotate, with approximately equal initial velocity, in a shell volume adjacent the inner walls of the container, with said shell volume having a predetermined thickness;

b) illuminating all the particles rotating within the shell volume with lighting means; and c) detecting at least one of light scatter, light reflection and light extinguishing caused by said particles, with detector means having a depth of focus of detection in which equally blurred images are viewed in opposite volumes of the container with respect to a plane through the axis of the container parallel to a plane through an imaging sensor;

wherein the sensed signal is corrected for the asymmetries of the imaging system by correction means either by computation or by repositioning the detector means relative to the container, whereby a focused imaging plane is formed at the container axis and then mechanically or electro-mechanically offset closer to the imaging sensor than the center of the cross section, whereby the size of detected particles in the opposite volumes is accurately mathematically compensatible to an actual size. The lighting means provides a multiplicity of directed lights, with said detector being masked relative to each of said lights, whereby each light illuminates symmetrical opposite volumes of the shell, with each volume being bounded by two opposing 90° arc segments of the container centered on and symmetrically disposed around the principal optical plane, (defined as a plane passing through the axis of the container, the center of the photo detector and normal to its sensing face).

The illumination sources (which also includes a single source with multiple sites of illumination) are symmetrically disposed around the vertical axis of the container, typically at an angle of 120° relative to each other and the light or photo detection sensors are disposed orthogonal (90°) relative to each other.

These and other objects, features and advantages of the present invention will become more evident from the following discussion and drawings in which:

DETAILED DESCRIPTION OF THE INVENTION, PREFERRED EMBODIMENT, AND THE DRAWINGS

Figure 1:
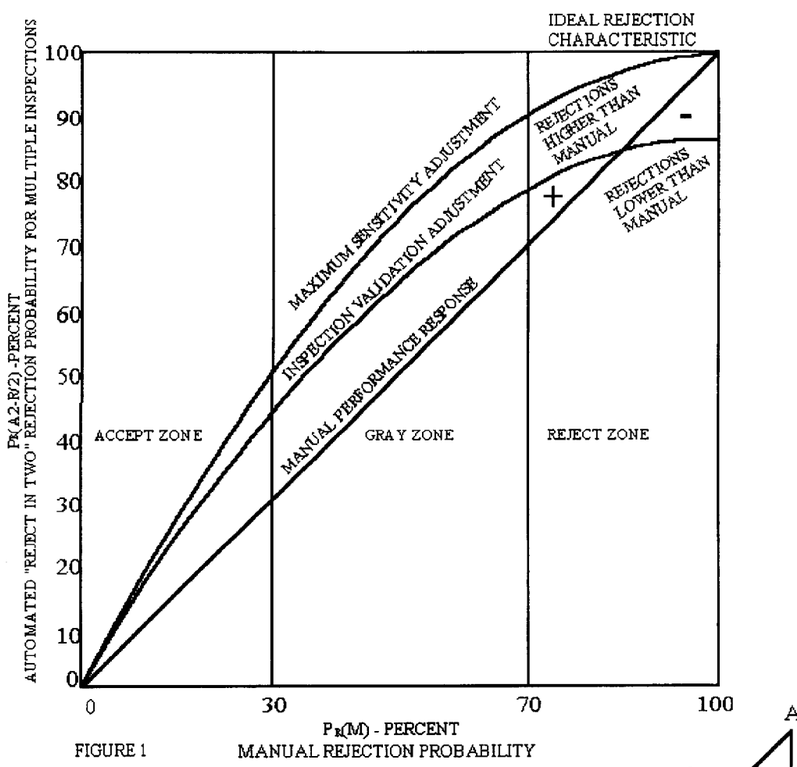
FIG. 1 is a graph showing the prior art probabilistic determination of particle contamination by typical manual and automated means as compared to an ideal full determination.

FIG. 1 of the drawings demonstrates the effect of the validation adjustment on present or prior art automated inspection system performance. To emphasize the effect of the inspection strategy employed, both the manual inspection reference and the maximum sensitivity adjustment curves are based on equal detection sensitivity. FIG. 1 compares the performance of the automated inspection to that of the non-ideal human inspection performance benchmark and an ideal rejection characteristic inspection, showing zero rejects for particle sizes less than the reject decision point (100 μm having been established) and a rejection probability of 1.00 for all larger particles.

Automated system performance curves that are higher than that of the straight-line human reference curve, exceed human performance. Wherever a performance curve lies under that of the human reference curve, a lower reject rate is indicated. Concerning the human performance reference curve, the manual rejection probability in the Accept and Gray Zones is an undesired, false reject rate. Any higher reject rate in these zones is even less desired.

The area under the manual inspection performance curve in the Reject Zone must be matched or exceeded in the validation demonstration of the proposed automation to show that an equivalent or higher inspection security has been achieved. An increased rejection capability in the Reject Zone shows improved security over that of the manual inspection. An ideal inspection characteristic would be rectangular: it would show zero rejections below the Reject Zone boundary and a rejection probability of 1.00 above the Reject Zone boundary.

The uppermost curve in FIG. 1 labeled 'Maximum sensitivity adjustment' matches the performance of the human inspectors for the rejection of those large particles most easily detected in human inspection. This is a group of containers with a manual rejection probability, PR(M) Of 1.00.

The improvement in particle detection security obtained by this 'reject in two' inspection technique is accompanied by a decrease in the selectivity of the accept/reject judgment. The excess economic cost of the maximum sensitivity adjustment is however too high for use. An alternative sensitivity adjustment (labeled "Inspection Validation Adjustment") validates the tested system by matching the net area under the manual inspection curve in the Reject Zone. The net area match is accomplished by a more secure inspection from the edge of the Reject Zone at 0.70 up to a rejection probability of 0.86 (shown as a cross-hatched area and marked with a plus sign) which is balanced by a security deficit from 0.86 to 1.00 rejection probability (shown as a cross-hatched area marked with a minus sign). When this validated inspection adjustment is used, a 4 to 6 fold increase in the rate of false rejects, compared to manual inspections, is usually experienced. This validated system minimizes human inspection time, but as FIG. 1 shows, a proportion of those rejects most easily detected by clinical personnel are passed through to stock.

In a preferred embodiment of the present invention, wherein the inspection follows the ideal, as depicted in FIG. 1, the following method steps are carried out.

Figure 2:
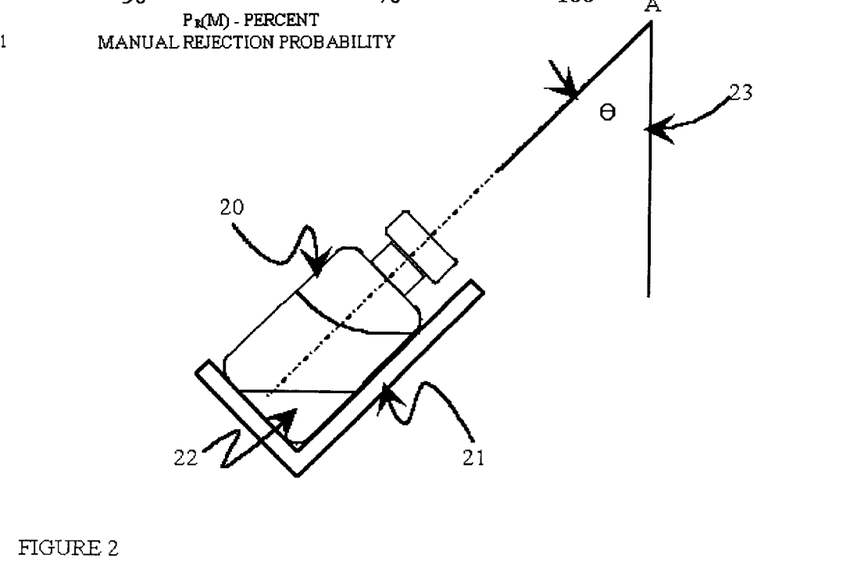
FIG. 2 shows a pre-positioning of particles within a container prior to inspection as used in the present invention.

The initial transport stages from container input to the inspection for particle contaminants are conducted using a rotational speed from 30 to 120 RPM to facilitate optical inspection of the cap, closure and the container body. Following these initial test positions, the container is translated, without rotation, in an inclined holder 21 at an inclined angle θ, as shown in FIG. 2. Any of the particles 1 in the container 20, whose density is greater than the supporting medium (i.e., which particles settle rather than float or are suspended in the supporting medium) are pre-positioned in the heel 22 of the container by gravity by a series of non-rotating translation steps. The container is progressively tilted at an angle between 15 and 75 degrees. The tilting terminates with the container being moved into a more upright or vertical position, with a tilt angle between 2 and 15 degrees for a trapezoidal rotational velocity pulse comprising a high speed and high acceleration rate stop followed by a single inspection.

The use of a tilt angle for the spin station displaces the center of gravity of the liquid from the spin axis. This displacement improves the coupling of the trapezoidal spin pulse to the container in the liquid by adding the coupling to the displaced liquid mass center to the skin drag coefficient available in the vertical spin position and thus to the particle within the container. The improved coupling increases the liquid cavitation threshold thus permitting higher acceleration and higher inspection rates.

The result of the trapezoidal rotational velocity pulse following the pre-positioning of all particles within the heel of the container is that the contaminating particles within the solution are contained and are spinning within the narrow tubular shell circumferentially adjacent the inner walls of the container.

The need for the transformation of the initial random particle distribution into a positioned array has been deduced from experimental measurements. In present art, the failure to detect randomly disposed larger particles in a single inspection following a spin and stop procedure is approximately 33%. Using a second spin reduces this random error to $(0.33)^2$ or 0.109. Three sequential spins prior to the inspection reduces this error to 0.0359. Pre-positioning the contaminating particles in the heel of the container and then using a trapezoidal rotational velocity pulse, a high acceleration rate to a selected rotational velocity followed by a high deceleration rate stop prior to the inspection reduces this single inspection random error. The failure to detect contaminating particles due to the random particle position approaches zero when the low speed, tilted pre-positioning sequence is followed by the trapezoidal rotational velocity pulse.

Figure 3:
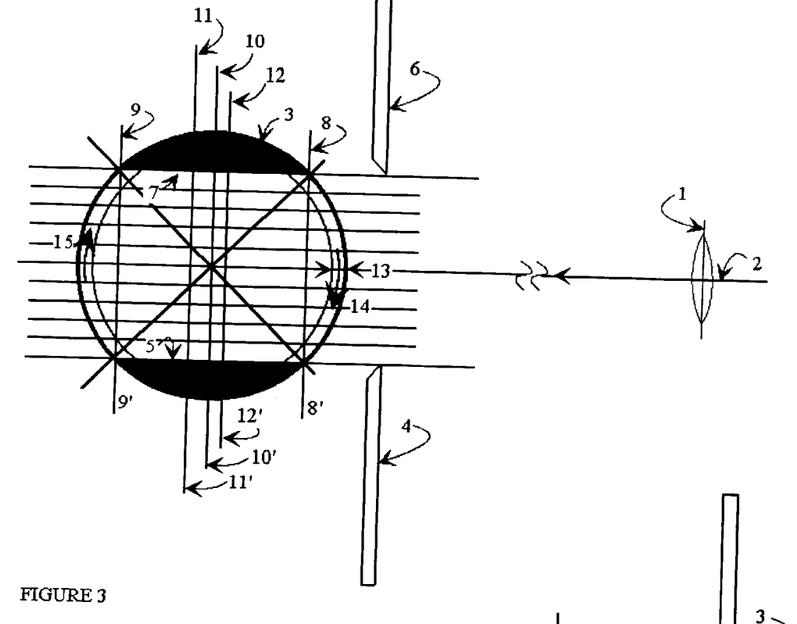
FIGS. 3 is a section of a container in a single axis particle inspection system showing the tubular shell volume in which the particles are contained, the vignetting used to restrict imaging to the central 0.7071 of the viewed image and the reversal of particle direction at the imager from the forward to the rear zone.

Important optical features of this invention are evidenced in the single axis inspection system of FIG. 3. The cross-sectional view shows the imaging lens 1 centered so that its axial ray 2 is centered between two vignettes 4 and 6, which limit imaging to the central 0.7071 of the container 3. The dotted area 7, between 45° and 135° and the similar dotted area 5, between −45° and −135° represent the inspection blinded volumes that lie between the front quadrants 8 and 8' and rear quadrants 9 and 9', with chordal planes that define the blinded inspection volumes resulting from single axis inspection. The initial focus planes 10 and 10', are adjusted to coincide with the axis of the container. This initial focus results in a displacement of the center of the Depth of Field to the planes 11 and 11' due to the asymmetry of the optical system, resulting in differently sized blurred images in the moving particle tubular containment volume 13. For particle sizing accuracy the images in the front and rear imaged zones are adjusted to equality by either separate calculations or by a shift of the plane of focus to positions 12, 12', at which equal blurred images for each crossing of the axial ray position are obtained. The vignetted particle inspection images are separated by their direction of travel in the imaged area. Particles in the near zone 14 are recorded as moving from right to left. Particles in the far zone 15 are recorded as moving from left to right. The inspected depth of field is adjusted to be equal to the predetermined container diameter by adjustment of the relative lens opening or the f stop. The inspection lenses 1 and 2 in the orthogonal inspection case and 1 in the single axis inspection case are adjusted to obtain focused images at the axis of the container. Adjustment is made to obtain equal blurred images in the shell volumes at closest and furthest distance to the imaging lenses in which the particles are spinning. The forward and rear portion are taken with respect to the axis of the container on the principal optical plane A, relative to the container walls, and the adjustments are made either by computation or by a mechanical or electromechanical shift of the focused plane to the 12, and 12' positions.

With the particle illumination detection by each of the detectors, and a position of the focused plane coinciding with the vertical axis of the container, separate formulas for size determination of particle blur images are utilized to compensate for particle position in either the near or far lens portion of the shell volume, during detection, with a size differential blur image, to thereby provide equalization of particle sizes (because of distance from the detector, particles in the far lens portion are measured by the detector as being smaller, though they may be of equal size). Repositioning the focus plane, as described, reduces the number of computations required for accurate particle sizing resulting in an improved inspection rate. When a single detector position is employed, the maximum inspection time required is that for the particle to go through the masked area and be detected for at least 5 scans.

The container or the detector is moved to position the focused plane away from the vertical axis of the container, to compensate for smaller depth of focus in the near portion of the shell with respect to the imaging lens.

The basic system optical description for each axis of the orthogonal inspection system is identical to the description of the single axis system described in FIG. 3. The essential difference is that the use of simultaneous orthogonal inspection eliminates the blinded volume inspection characteristic of a single axis inspection system. This can be seen in FIG. 4, wherein the axial rays of the two orthogonal detectors 1 and 2 and their corresponding vignettes are each positioned to permit viewing of the central 0.7071 of the container image. The axial rays for each detector each pass perpendicularly through the axis of the container, relative to the respective detectors, to inspect a tubular container volume bounded by opposing 90 degree arc segments of the container, symmetrically distributed around the principal optical plane, in the near and far parts of the shell volume with respect to the viewing means.

Figure 4:
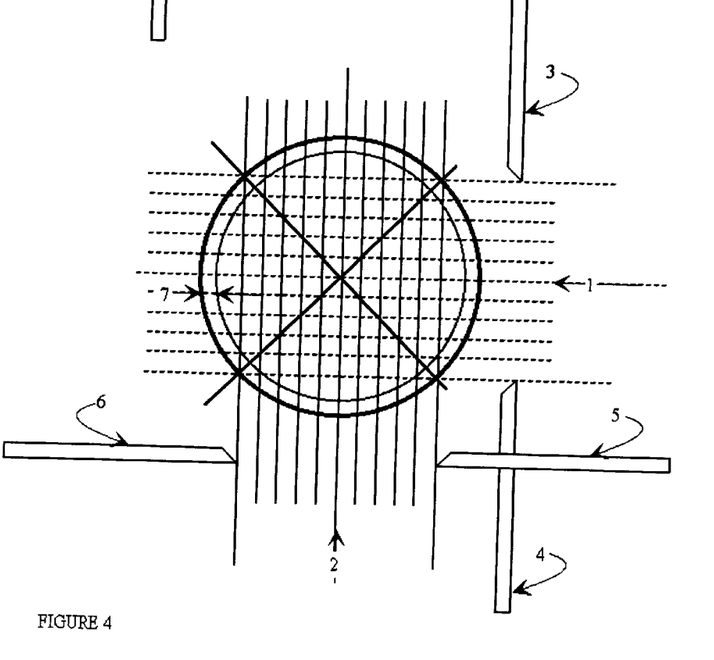
FIG. 4 illustrates the use of orthogonally directed viewing to image the total volume of a container with a cross section of the container.

Container quadrant chords bound the ends of the 90° arc volume segments which are inspected. The chords are the bases of isosceles triangles whose central container angles are 90° and whose altitudes commence at the container vertical axis and are perpendicular to the principal optical plane.

The remaining portion of the shell is masked off to detection by one of the detectors and is adapted for detection by the other orthogonal detector. With the two detectors so positioned, the full volume of the shell and the particles contained thereon are deterministically and not merely probabilistically detected. The inspection scan time is preferably sufficient for 5 scans of a particle when orthogonal viewing is used.

When mechanical repositioning of the focus plane is not employed, determination of whether particles are in the front or rear portion of the shell, for applying the formulas, is effected by determining the sequence of movement of the individual particles with front and rear positioned particles moving in opposite arced directions.

The plane positions of the particles, i.e., the position of the particle within the 90° arc (±45° from the axis of the container) but offset from the detector axis by the imaging distance are determined by trigonometric relations defined in the plane, i.e., sine function, in conjunction with particle movement. The position obtained is used to correlate actual blur particle size detection to a corrected size. Proper resolution in the above determines particle size, to reduce rejects to the particular particle size used as the reference for rejection.

The light source is provided with intensity stabilization means, such as a feedback loop which samples the average light intensity produced. Pixel by pixel normalization of the intensity of the image light flux is then effected with a systematic process in which the light intensity at each pixel is compared to its neighbors.

Pre-Positioning of Particles

With reference to the above, in the present invention, greater accuracy in detection of particles is achieved by changing the detection of randomly positioned particles in the full volume of injectable products to the detection of all the particles within a defined portion of the container. As described, this transformation is begun by pre-positioning the contaminating particles within the heel of an axially inclined container, prior to any further action, as taught in one of the inventors' U.S. Pat. No. 5,694,221, issued Dec. 2, 1997, the disclosure of which is included herein by reference thereto. This patent teaches that, by using time and gravity, contaminating particles can be segregated into the heel of a container in a position inclined to the vertical axis. Spinning the container around its vertical height axis in a position inclined to the vertical, decreases the time required for transfer of rotational velocity to the enclosed liquid. This is due to the displacement of the center of gravity of the liquid from the rotational axis of the container to assist the drag coefficient in generating the desired liquid rotational velocity and the uniform particle orbital velocity without cavitation in a short trapezoidal velocity pulse.

The result of particle prepositioning, prior to the high speed spin and stop sequence employed, is the substantially uniform centrifugation of the contaminating particles into tubular volumes (or shells) adjacent to the container walls. As a result, particle orbital velocities within the container are all within an accurately defined band. The particles rotate around the vertical axis of the container in orbits adjacent to the container walls.

Determination of Particle Size (with Single Viewing Axis)

An important prerequisite for particle measurement in sealed pharmaceutical containers is the accurate determination of the size of a contaminating particle. Exact direct particle size determination is not logistically feasible with current technology. However, in view of the prior art teaching that blur images (images with blur fringe) are size consistent and the actual particle size can be correlated thereto, in accordance with the present invention, the blur images are corrected for size variations resulting from detected signals with positional variations. This is effected by determination of particle position and motion. Thus, the imaged particle size and its blur fringe vary as the orbital movement of the particle varies its position with respect to the imaging optics. Methodology to control the maximum amount of particle signal blur and to adjust all particle signals for an equally blurred image prior to determination of particle size is described hereinafter. This correction method provides additional means to make possible more accurate sizing and counting of contaminating particles in pharmaceutical containers.

The image correction methodology commences with the imposition of defined orbital movements on the contaminating particles and appropriate selection of the orbital segments of particle travel for analysis. The combination of these two actions provide the basis for the extraction of accurately sized contaminating particle signals for container volumes which goes beyond the sharp imaging capability of present lenses.

In order to define the position of a given particle with respect to the imaging lens, in accordance with the present invention, an imaging lens adjustment is made to provide a focused plane (10, 10' in FIG. 3, relative to the light sources and detectors) through the vertical axis of a container parallel to the image plane to view the orbiting particles in the shell. With this adjustment, the complete range of particle image size variation is defined. Due to the asymmetry of the imaging lens, the center of the Depth Of Field is offset from the focused plane as shown by the 11, 11' planes in FIG. 3. Following the re-positioning of the focused plane to a point between the container vertical axis and the imaging plane at the face of the CCD array employed plane 12, 12', there are two orbital positions in which the blur fringe for a particle is of a maximum value and is equal in size. These two positions occur when the particle orbit enters and transits the principal plane of the system. These particle positions lie at an angle of ±90° relative to the focused plane through the container axis. The principal plane is a plane through the axis of the inspected container that is perpendicular to the imaging surface.

Particle sizing equations differ for the particle orbital segments at each side of the focused plane. Successful use of these equations for particle sizing at these two maximum orbital points, and for any other point in the orbital trajectory of the particle, require information concerning the position of the particle with respect to the focused plane. In accordance with the present invention, accurate sizing of a particle can be accomplished for any particle position within the container. To achieve efficient particle sizing, the imaged width of the inspected container is vignetted to control the particle sizing error due to orbital rotation of the particle and the optical properties of the container and with limiting imaging to the container volume bounded by two opposing 90° arc segments of the container, symmetrically disposed around the principal optical plane. Container quadrant chords bound the ends of the inspected volume within each of the 90° arc segments. The chords are the bases of isosceles triangles whose central container angles are 90° and whose altitudes commence at the container vertical axis and are perpendicular to the principal optical plane.

Restricting particle inspection to the viewed volume limits particle sizing variability to a maximum of −29.2% when compensation for the angular position of the particle within its orbit is not employed. The volume viewing limit corresponds to viewing the central 0.7071 of the container image. This adjustment requires an extension of inspection time for worst case blinded particle travel through 90° and accomplishment of a minimum of 5 scans. With a dual tap progressive scan, the duration of each full scan is 16.67 milliseconds. A scan of the bottom half of the container, with current technology, is accomplished in 8.34 milliseconds. The rotational velocity of a particle at the start of an inspection is under experimental control. As an example, adjusting the particle rotational velocity to one orbit in 400 milliseconds results in contaminating particles traversing a 90° arc in 100 milliseconds. Since orbital travel of a particle and camera scan times are asynchronous, estimates must include a buffer of 1 scan time at the start of each 90° sector inspection. Accordingly, 2½ scans of the lower half of the container followed by 5 full image scans can be securely completed in the 100 millisecond inspection time available for a 90° sector in the smallest container examined. This scan sequence is selected to assure adequate detection time for the heaviest particles whose friction against the container walls results in the shortest movement time. The minimum inspection period for secure results with a single axis camera is therefore equal to the ¼ particle orbit time, in which the particle is vignetted from view, and the 100 millisecond particle inspection imaging time, for a total of 200 milliseconds. This is an inspection rate of 300 containers per minute with secure, deterministic inspection results. This inspection speed is possible based on the capability to image the full depth of the container and pre-positioning the particle before the spin cycle is defined. FIG. 4 illustrates these limits and particle vignetting.

Calibration of Particle Size and Blur Images

When the imaging system is adjusted so that the focused plane coincides with the vertical axis of the container, the asymmetry of the imaging system limits sizing accuracy. The size of the blur fringes surrounding a particle image is determined by the particle position in the container with respect to the focused plane. The blur fringe and its onset gradient for particles closer to the imaging lens than the focused plane are different from those in the container volume beyond the focused plane. Particle sizing accuracy is improved when the particle blur fringe is adjusted to equality before the particle sizing process is implemented. Particle sizing correction may be implemented by calculation, comparison of the particle signal and size determination from stored calibration data or by off-setting of the focused plane to achieve equal blurred images on both sides of the container vertical axis.

To achieve particle detection reliability approaching 100%, the liquid volume containing the particle must revolve through the inspected volume. As the size of the inspected container increases, the effect of the blinded inspection time on the total secure inspection time becomes increasingly significant. A more time efficient approach for the inspection of larger container sizes is the use of dynamic particle sizing based on symmetrical blurred images on each side of the container axis. The use of a single sensor reduces system cost and complexity, but requires adequate rotational velocity transfer to the particles and an extension of the inspection period to ensure that the total liquid contents rotate through the detection zone and have been inspected.

Orthogonal Viewing Axes

In accordance with the present invention, the total time for secure container inspection is reduced when orthogonal viewing axes with a depth of focus equal to the container diameter and blur signals are adjusted to equality are employed to make the inspection. The use of orthogonal viewing axes with each view restricted to the central 0.7071 of the container diameter provides a full view of the container volume and the orbital tracks followed by the contaminating particles within the container. The use of orthogonal viewing axes results in a constant, secure inspection time, independent of container size.

Each imaged segment of the particle orbit lies within a 90° arc section of the container symmetrically positioned around the central plane of the imager at 0° and 180° from the viewing means reference position. This is the plane that includes the axis of the container and is perpendicular to the surface of the CCD used in a detector. There is a direct correspondence between the angular position of a particle in its visible orbital track and its imaged position in the width of the CCD. The maximum size variation resulting from the ±45° particle movement around the principal plane of the system is a blur fringe variation of 30%.

Sizing accuracy is maintained when the energy contained in the blur fringe is combined with the primary energy in the partially focused particle.

Analysis of Single Particle Signals

The container is spun in a clockwise direction prior to inspection and the resulting particle movement is strongly horizontal. The object field is vignetted to the central 0.7071 of the container image, resulting in a separation of orbital particle image movement in the container into clockwise and counter-clockwise movement categories. A particle moving in the clockwise direction is in the orbital sector (shell volume segment) closer than the focus plane to the imaging lens. A particle moving in the counter clockwise direction is in the orbital sector further than the focus plane from the imaging lens. The asymmetric imaging resulting from the imaging lens, with particle images between the container axis and the imaging lens appearing smaller than particle images further than the container axis from the imaging lens. For good measurement accuracy, generation or calculation of equal images is required. To achieve this end three methods are described. The first uses a calculation sequence that is different for the near and far zone particle signals. Employment of this method uses a sequence of closely spaced particle images assembled in memory which will therefore identify particle movements on each side of the focused object plane. The determination to use the expression for NEAR or FAR to correct the sensed particle size (in the near or far sectors respectively) is made after a determination of the direction of horizontal movement is made from a stored sequence of particle signals which locates the segment in which the particle is located, when detected.

Correction for the Angular Position of the Particle

By inspection, the near and far angular particle positions, for maximum blur, occur at the points of closest and furthest distance from the focused plane through the container axis. These points are at the particle orbital intercept positions with the central plane of the imager at 0° and 180° from the viewing means reference position. Determination of the distance of the particle from the focused plane for any position in its imaged traverse is used to correct the imaged particle size.

Measurement of the projection of the centroid of the particle image on the CCD array provides the information required to calculate the relative position of the particle within the container. This measurement determines the displacement of the particle with respect to the central object plane through the axis of the container and is used to determine the size of the blur for any position of the particle within the vignetted image analyzed.

As exemplified in FIG. 4, the ratio of the horizontal displacement of the centroid of the imaged particle from the center of the CCD array to the inner radius of the container is equal to $Cos^{-1}$ of the central angle D, of the orbital position of the particle. Sine D is calculated as the square root of 1 minus $(COS^2 (D))$. The product of the Sine D and the internal radius of the container determines the object plane in which the particle has been imaged. Twice the product of Sine D and the inner radius of the container is the depth of field. Determination of the blur fringe for the calculated depth of field then follows.

The dynamic correction in the size of the blur fringe results in accurate particle size measurement for any particle in the vignetted field of view. An alternative to the evaluation of the size of the image blur on which to base particle size correction, is to detect the maximum blurred image for which a constant particle size correction can be stored in memory. This dynamic correction method is of particular value for use with orthogonal viewing axes and eliminates the need for the extension of inspection time associated with particle size peak detection. Accurate particle size measurement is obtained from light flux measurements of blurred particle images. Physically based particle sizing is accomplished with the stable characteristics of the imaging lens, combined with the stable physical size of an image transduction array.

A more time efficient method of image correction commences with a focused plane through the vertical axis of the container and then, either mechanical or electro mechanical means is used to offset the position of the focused plane, to achieve equal blurred images, at the image transduction array at both orbital travel extremes, with respect to the imaging lens.

It is generally accepted that the clinical hazard from contaminating particles is size dependent. The available automated inspection systems calculate an equivalent spherical diameter from the maximum projected image of a particle randomly positioned with respect to the imaging plane. Non-spherical particles including platelet and fiber particle types are presently grossly undersized in this type of measurement.

In the present invention, pre-positioning of the contaminating particle, using gravity and time, results in maximum rotational force on the particle during the spin cycle. Rotational and hydro-dynamic force orients the particle for measurement. The vignetted restriction of the contaminating particle size measurement defines the variability expected in the particle size determination. An alternative, more time efficient and more time efficient sizing procedure uses displacement of the focused plane to measure the size of symmetrically blurred images.

The inspection capability resulting from the described improvements makes it possible to achieve a single, validatable inspection, rather than the two-inspection sequence currently employed. The important benefits from application of this disclosure are an improved inspection security, containers with visible particles are securely rejected and the present rate of false rejects are reduced. The duration of the inspection for secure results is determined from the initial orbital velocity of the contaminating particles. The worst-case inspection time with a single camera is determined by the time required for a 25% orbital path and a total of 6 CCD scans. This worst-case single axis inspection time has been experimentally determined to be in the range from 200 milliseconds for 5 ml containers up to 1 second for the inspection of 1 L containers. An inspection system employing two cameras in orthogonal positions can achieve the same inspection security in a constant inspection time of 100 milliseconds, independent of container size.

Stabilization of the Detection System

A highly preferred feature of the present invention is the providing of a method of detecting light flux particle signals that minimize the effect of point-to-point illumination variation within the inspection volume. In the present invention, the particle sizing accuracy and the stability of particle inspection results are improved by the following:

1) The measurement capability of the system is stabilized by the use of a light source whose intensity is stabilized by a feedback loop that samples the average light intensity produced.

2) Pixel by pixel normalization of the intensity of the image light flux improves particle sizing accuracy. This normalization minimizes the effect of illuminance variability from the source, from optical defects and markings on the container and provides equal detectability for low and high contrast particles with a single light source.

The measurement stabilization described above makes possible an economically achievable flux based measurement of particle size. A significant improvement in particle signal to noise ratio is achieved with the use of the restricted area signal measurement as described below.

Physical Sizing of Contaminating Particles

As taught in U.S. Pat. No. 5,365,343, issued Nov. 15, 1994, the total light flux collected from the particle signal and its blur fringe is substantially constant for a variation of 470% in the relative size of the blurred particle image to its sharply focused size. Following the detection of a signal anomaly, the position of its flux centroid is calculated with successive hollow squares being generated. Commencing with a hollow 3×3 array, successive larger hollow arrays are tested until a signal flux area is defined. The edge of the signal flux area is detected as a 3 to 30% flux drop in the smoothed flux versus blur ring edge. The requirement for interpolation between calibration points is established with this curve. For approximately spherical particles, the summed area representing the particle and its blur fringe is equated to the projected image of an equivalent sphere. The processed data recorded for each particle is the diameter of the equivalent sphere without its blur fringe.

The smallest calibrated particle size is determined by the product of the reduction factor, R, and the size of a pixel, P, in the imaging CCD. The minimum imaged field for the smallest calibrated particle size is the sum of the imaged pixel and its equal blur fringe. The system is adjusted to generate a maximum, equal, single pixel blur fringe for all particle sizes. Particle size measurement accuracy for single pixel measurements is maintained down to 99.4 $\mu$m, the 50% signal level for single pixel measurements at a reduction factor of 19. This is a limit imposed by signal to noise considerations which minimizes the sensitivity of the inspection system to the minor operating point shifts that always occur in daily use. The unprocessed video signals and the blur size corrected particle image are overlaid to provide real time monitoring of particle sizes and shapes.

Image Illumination Normalization

A limiting factor in the detection of a contaminating particle is the ability of the detection system to distinguish a change in any point of the illuminated image. The usual mechanism for detecting this change is to test for differences from the average scene illumination. Major effort is being expended in responding to this problem, in the production of an even illumination level across the entire viewed object. When the contents of a container are inspected for particle contaminants, residual variability of illumination, local optical marks and defects and the curvature of the container itself combine to defeat any attempt at tightly specified image evaluation and thus limit particle detection capability.

The image processing in the present invention normalizes the light flux on each pixel of the viewed container with respect to its immediate environment. In this process, the determination that a particle signal has appeared at a specific point is made by comparing the light flux at that point with respect to the light flux sensed on all the surrounding pixels.

Light Flux Based Particle Sizing

In an embodiment of the present invention, gray scale values are used as a measure of the amount of energy of the image at each pixel of the image detection sensor. Scene normalization is realized in a three step sequence. The first step in this process is the division of the sensing area into squares whose size is determined by the largest contaminant that could be detected. The size of these "Max-Box" squares usually varies between 0.20 and 1.00 mm. The average image intensity in each Max-Box square is evaluated and recorded in the memory position assigned to the upper right pixel in a square group of four pixels closest to the geometric center of the Max-Box square.

In the second step, the sensing area is divided into squares representing the smallest particle size to be evaluated, the Min_Box square. The average illumination intensity on the Min-Box square is determined and recorded in the memory position assigned to the upper right pixel in a 3×3 square group of pixels closest to the geometric center of the Min-Box square. The minimum value of the Min-Box square is a 3 by 3 pixel array.

The last step in the sizing sequence is to subtract the processed image from the original image. The result is a "Difference" image which yields a gray scale representation of the contaminating particle. The gray scale value of the particle image is equal to the difference between the particle and the normalized value of the background illumination.

This image normalization makes possible accurate detection of low contrast particulates by reducing the burden of image illumination variation with a major increase in performance over that of human vision. It makes available the extended gray scale sensitivity of the CCD array, a factor of 12.8 times more sensitive for the usual low contrast particles encountered in well controlled pharmaceutical manufacturing.

This normalization procedure provides an improvement in the processing of particle signals. The detection of particle images is a dynamic process and is affected by the designed variation in acceptable blur fringe and the departure from a spherical shape. The maximum particle size detected throughout the tracked orbit is determined in a skeletonization analysis of the particle shape. This procedure tests for image connectivity in a string 1 pixel wide. The usually encountered range of fiber diameters is 2 to 10 $\mu$m, the length of the fiber contaminants can range up to millimeters. The capability to securely distinguish and reject containers and to report on the sized inventory of contaminating particles in containers is possible. This inventory of contaminants is useful in particle contamination control in injectable preparations.

The tracking detection strategy is appropriate for the low concentration contaminants typical of visual contaminants in pharmaceutical products. Supplementing this visual particle size detection strategy is the evaluation of the average gray scale of the Max-Box image data for the detection of the appearance of haze or of particle concentrations too numerous to allow individual tracking orbits.

The sequence of operations described results in a particle detection system with maximum accuracy at the accept/reject threshold. This is desirable since it provides a yes/no rejection characteristic based on particle size even in a single comparison for a particle that is in the field of view. The Max-Box size is proportioned to make possible maximum particle size measurements with sizing error under 1% when five sequential images are detected.

The Max-Box square size is determined to be a multiple of the largest particle to be accurately sized. In this case it is the 1,058.2 $\mu$m particle and the Max-Box is chosen to be twice as large, 2,116.4×2.116.4 $\mu$m.

The Min-Box size is determined by the minimum square array that will contain the smallest particle of interest and its blur circle. In this case the diameter is equal to the sum of the smallest calibrated particle of interest, 140.6.8 $\mu$m and twice the 140.6$\mu$m blur fringe, a total of 421.8 $\mu$m. To fit the total of 88.8 $\mu$m particle diameter and its 88.8 $\mu$m blur fringe onto a 3×3 array of 7.4 $\mu$m pixels requires a reduction ratio of 19. The calibrated particle size plus blur fringe for a typical system, based on the stable optical properties of the imaging lens and the physical size of the CCD pixels, are listed in Table 5.

Accept/Reject Decision Boundary

In all present non-destructive inspection systems the boundary between accept and reject contamination quality is diffuse and is indirectly determined. The most widely used determination is based on the average rejection probability of a group of containers determined in the human inspection to be of 'must reject' quality. Holographic measurements in the prior art determined the particle size at the accept/reject boundary to be 100 $\mu$m, which threshold size can be adjusted.

In any measurement system, optimum measurement accuracy is found at calibration points. In this inspection system, the particle size selected to define the boundary between the accept/reject quality zones can be used as a physically determined calibration point. The particle size at the calibration points is determined by the stable optical characteristic of the imaging lens and by the size of the imaging pixel array. In the following example, the 140.6 $\mu$m particle size is used as the first calibration point. This choice combines the nearly ideal binary accept/reject decision capability with a stable, physically determined particle size reference. The minimum accurately measured particle size with this calibration scale is 99.4 $\mu$m, Although 99.4 $\mu$m has been used in this example, the particle size selected as the boundary size is only an illustrative design choice.

To achieve best sizing accuracy in the interpolated sizes between calibration points, a stabilized light source is essential. The regulation for this light source must be based on a stable fraction of the emitted light. Any attempt to use either voltage or current regulation as an indirect way of controlling the amount of emitted light does not include the variation in the lamp employed and thus cannot maintain control of the emitted light level.

EXAMPLES

In order to illustrate the efficacy of the present invention, the following examples are disclosed. Details contained therein are not to be construed as limitations on the present invention.

Summary of the Geometric Optic Relationships Employed

As is well known in geometric optics, the distance between the object, O and its image, I, in terms of the object/image reduction ratio, R, and the focal length of the lens, F, is defined in Eq. 1.

$$O + I = \frac{F(R+1)^2}{R} \quad \text{Eq. 1}$$

The particle size imaged on a single pixel, P, is determined by the size of the pixel, p, and the selected imaging reduction ratio.

$$P = Rp \quad \text{Eq. 2}$$

The depth of field, DOF, in which an image with a selected blur fringe is seen is symbolized as T in Eq. 3.

$$T = 2NpR(R+1) \quad \text{Eq. 3}$$

R=object to image reduction ratio
pR=blur size as a multiple of the sensor pixel size, p.
N=relative lens opening
F=focal length of lens The asymmetry of the imaging system results in a displacement of the center of the depth of field away from the imaging plane. Prior to any correction, the focused plane moves a distance $\Delta$ beyond the vertical axis of the container away from the image plane. The asymmetry of the imaging system provides a greater imaging depth for the container volume furthest from the imaging means. For measurement accuracy, compensation for this asymmetry is required. This can be accomplished either by calculation as described, or by readjustment of the position of the focused plane with respect to the vertical axis of the container.

$$\Delta = \frac{2N^2(pR)^2(R+1)}{F} \quad \text{Eq. 4}$$

The required displacement of the focused plane for equally blurred images at the sensor, $\delta$, is ½ of the shift calculated with Eq. 4. The shift is taken toward the zone behind the axis of the container, away from the lens position. The required displacement, Δ/2 is calculated with Eq. 5 and is symbolized as δ.

$$\delta = \frac{N^2(pR)^2(R+1)}{F} \quad \text{Eq. 5}$$

Equations 4 and 5 are evaluated for the selected reduction factor in Equations 6 and 7. Calculation of the particle size imaged on a single pixel is shown in Eq. 6.

$$T=5.6240N \quad \text{Eq. 6}$$

The shift of the focused plane from the vertical axis of the container for blur symmetry of particle images at the closest and furthest orbital position to the imaging transducer for an image reduction factor of 19 is determined by substituting the selected parameters into Eq. 5 as shown in Eq. 7.

$$\delta=0.01419N^2 \quad \text{Eq. 7}$$

The image of the particle, I(P), on a single pixel, p, is the product of R, the image reduction ratio, 19 and the pixel size, 0.0074, is equal to 140.6 μm as shown in Eq. 8. The single pixel ½ signal level particle size is calculated with Eq. 9 and is 99.41 μm.

$$I(P)=pR=0.0074\times19=140.6 \, \mu m \quad \text{Eq. 8}$$

The following inspection system design maintains constant particle size sensitivity for the range of injectable product containers from 1 ml to 1 L. Table 1 shows that an object to image reduction ratio of 19, containers from 1 to 250 ml can be imaged on a single ⅓ inch, 4.87×3.67 mm CCD. This CCD has 0.0074 mm square pixels in a 768H×494V array. The distance between the container vertical axis and the imaging CCD with a 25 mm focal length lens, before any adjustment of the focused plane, calculated with Eq. 1 is 526.32 mm. In each case the major chip dimension is oriented in the vertical position. The particle size for full signal on a single pixel is 141 μm, at ½ full signal 99.4μm particles are sized with good accuracy. Vignetting is used to limit the imagers view to the central, horizontal 0.7071 of each container and the liquid fill height. Two CCD arrays are used in a vertical array for the 500 ml and the 1 Liter containers.

TABLE 1

CONTAINER COVERAGE AT AN IMAGE/OBJECT REDUCTION RATIO OF 19.

| CONTAINER VOLUME, mL | AREA IMAGED | CCD ARRAY V × H |
|---|---|---|
| 1–250 | VERTICAL, 92.5 mm HORIZONTAL, 69.7 mm | 1 × 1 |
| 500 ml, 1 L | VERTICAL, 185.0 mm HORIZONTAL, 69.7 mm | 2 × 1 |

The ⅓ inch, 4.87×3.67 mm CCD used for this illustrative, non limiting example has 0.0074 mm square pixels in a 768H×494V array. The focused distance, prior to depth of field correction, between container axis and the imaging CCD with a 25 mm focal length lens calculated with Eq. 1 is 526.32 mm. In each case the major chip dimension is oriented in the vertical position. The particle size for full signal on a single pixel is 141 μm, at ½ full signal 99.4 μm particles are sized with good accuracy.

Maintenance of constant particle size detection results is accomplished with the use of a single CCD for containers from 1 to 250 ml volume capacity. Vignetting is used to limit the imagers view to the central, horizontal 0.7071 of each container. Two CCD arrays are used in a vertical array for the 500 ml and the 1 Liter containers.

Table 2 illustrates control of the Depth of Field through manipulation of the relative lens opening for the full container range from 1 ml to 1 L. Table 2 also lists the focused plane shift from 0.061 mm to 4.995 mm, depending on the imaged container, required to achieve equal blurred images on both sides of the vertical container axis with respect to the imaging lens.

TABLE 2

DEPTH OF FIELD AND FOCUS PLANE SHIFT FOR AN OBJECT/IMAGE REDUCTION RATIO OF 19

| Container D.O.F., mm Container, | Diameter = D.O.F., mm | Scanned Width = .707 D.O.F., mm | Liquid Height mm | Relative Lens Opening, f# | Plane Shift Between Lens & Container Axis δ, mm |
|---|---|---|---|---|---|
| 1 | 11 | 7.7 | 11 | 1.96 | 0.061 |
| 2. | 15 | 10.7 | 15 | 2.67 | 0.113 |
| 3.5 | 16 | 11.2 | 17.5 | 2.84 | 0.127 |
| 5 | 21 | 14.7 | 14.5 | 3.73 | 0.220 |
| 10 | 23 | 16.1 | 24 | 4.09 | 0.265 |
| 20 | 28 | 19.6 | 32.5 | 4.98 | 0.392 |
| 30 | 28 | 19.6 | 62 | 4.98 | 0.392 |
| 50 | 40 | 28 | 45 | 7.11 | 0.799 |
| 100 | 48 | 33.6 | 52 | 8.53 | 1.151 |
| 250 | 60 | 42 | 90 | 10.67 | 1.800 |
| 500 | 80 | 56 | 100 | 14.22 | 3.198 |
| 1 L | 100 | 70 | 140 | 17.78 | 4.955 |

At a reduction ratio of 19, the single full single pixel particle image is 140.6 μm. The ½ full pixel particle size is 99.41 μm. With orthogonal viewing axes, the inspection time for each container listed is constant at 100 milliseconds.

Table 3 illustrates an improvement in signal, as shown by smaller f numbers, with a change in object/image reduction ratio from 19 to 24. With this change. the single pixel particle image increases from 140.6 μm to 177.6 μm: the equivalent ½ signal particle size is 125.6 μm.

TABLE 3

DEPTH OF FIELD AND FOCUS PLANE SHIFT FOR AN INCREASE OF THE OBJECT/IMAGE REDUCTION RATIO FROM 19 TO 24.

| Container | | | | Relative | Focus Plane |
|---|---|---|---|---|---|
| Volume ml | Diameter = D.O.F. mm | Scanned Width 0.707 D.O.F. mm | Liquid Height mm | Lens Opening f# | Shift δ mm |
| 250 | 60 | 42 | 90 | 6.78 | 1.450 |
| 500 | 80 | 56 | 100 | 9.01 | 2.561 |
| 1 L | 100 | 70 | 140 | 11.26 | 4.000 |

Improvement of signal levels in the inspection of the Large Volume Parenteral containers with current technology is achieved by an increase of the single pixel imaged particle size from 140.6 μm to 177.6 μm. The ½ signal single pixel particle size accordingly increases to 125.6 μm.

Table 4 demonstrates the inspection timing and rate achieved by the use of a single axis inspection system. Clearly seen here is the decrease in inspection rate due to the time required for worst-case blinded particle travel as container size increases. For many smaller containers the time increase required for single axis inspection still results in acceptable rates. The 1 Liter inspection time increases 6 fold.

TABLE 4

SECURE SINGLE AXIS CONTAINER INSPECTIONS

| CONTAINER VOLUME, ML | 90° BLINDED TRAVEL TIME MILLISECONDS | SECURE INSPECTION TIME MILLISECONDS | SECURE INSPECTION RATE PER MINUTE |
|---|---|---|---|
| 5 | 100 | 200 | 300 |
| 10 | 110 | 210 | 286 |
| 20 | 115 | 215 | 280 |
| 30 | 115 | 215 | 280 |
| 50 | 200 | 300 | 200 |
| 100 | 240 | 340 | 176 |
| 250 | 300 | 400 | 150 |
| 500 | 400 | 500 | 120 |
| 1L | 500 | 600 | 100 |

Single axis inspection time for secure container inspections is determined as the sum of the blinded 90° transit time and the 100 millisecond inspection time specified. The time extension required for a secure single axis inspection of injectable product containers compensates for the worst case blinded orbital travel time in each container size.

Table 5 illustrates pixel assignment at an object/image reduction factor of 19. The calibrated particle sizes for this system are based on the stable optical properties of the imaging lens and the physical size of the CCD pixels.

TABLE 5

CCD PIXEL ARRAY USE WITH A REDUCTION FACTOR OF 19 PIXEL ASSIGNMENTS IN THE IMAGING PLANE CALIBRATION CURVE DATA

| Po | 2B | SUM | PIXEL ARRAY |
|---|---|---|---|
| 140.6 | 281.2 | 421.8 | 3 × 3 |
| 281.2 | 281.2 | 562.4 | 4 × 4 |
| 421.8 | 281.2 | 703.0 | 5 × 5 |
| 562.4 | 281.2 | 843.6 | 6 × 6 |
| 703.0 | 281.2 | 984.2 | 7 × 7 |
| 843.6 | 281.2 | 1,124.8 | 8 × 8 |
| 984.2 | 281.2 | 1,265.4 | 9 × 9 |
| 1,124.8 | 281.2 | 1,406.0 | 10 × 10 |
| 1,265.4 | 281.2 | 1,286.6 | 11 × 11 |
| 1,406.0 | 281.2 | 1,687.2 | 12 × 12 |

Particle size is a function of the CCD pixel array in a ⅓ inch CCD with 7.4×7.41 $\mu$m pixels for the inspection of containers from 1 m to 1 L. The object to image reduction ratio R, is 19. When a 25 mm focal length lens is used, the distance between the face of the CCD and the imaging lens is 526.32 mm. This distance remains constant after adjustment for equal blurred images.

The design flexibility with the concepts described herein makes possible a single design with constant particle size resolution for all injectable container sizes between 1 ml to 1 L and improved, constant particle size resolution for a restricted range of container sizes. Two examples are considered: a container size range between 10 and 30 ml and a container size range from 10 to 100 ml.

When a container size range between 10 and 30 ml is selected, an object/image reduction ratio of 13 provides an increase of resolution in which 96.2 $\mu$m is imaged on a single pixel, the ½ signal level provides good sizing down to 68 $\mu$m. At this object/image reduction ratio 29.6 mm Depth Of Field is obtained when a relative lens opening f=11 is used.

When a container size range between 10 and 100 ml is selected, an object/image reduction ratio of 17 provides resolution in which 140.6 $\mu$m is imaged on a single pixel, the ½ signal level for this object/image reduction ratio provides good sizing down to 89.0 $\mu$m. At this object/image reduction ratio 49.8 mm Depth Of Field is obtained when a relative lens opening f=11 is used.

What is claimed is:

1. A method for the substantially complete detection of all particles, within a predetermined size range, contained in an injectable solution, in a transparent container therefor, said method comprising the steps of:

a) pre-positioning particles in the container whereby rotation of the container causes substantially all of the particles in the injectable solution in the container to rotate in a shell volume adjacent the inner walls of the container, with said shell volume having a predetermined thickness;

b) illuminating all the particles rotating within the shell volume with lighting means; and c) detecting at least one of light scatter, light reflection and light extinction caused by said particles, with detector means having a depth of focus of detection in opposite volumes of the shell along a cross sectional diameter of the container;

wherein detector means is positioned, relative to the container whereby a focal point of detection coincides with the center of the cross sectional diameter, whereby the size of detected particles in the opposite volumes is accurately mathematically compensatable to an actual size; and wherein said lighting means provides at least two directed lights, spaced 120° from each other, with said container being masked relative to each of said lights whereby each light illuminates different opposite volumes of the shell, with each of the opposite volumes being bounded by two opposing 90° arc segments of the container, symmetrically disposed around the principal optical plane, which optical plane is normal to the respective sensing faces of the photo detectors and perpendicular to the surface of each detector means, and wherein the said inspected volumes are further bounded by two container quadrant chords which connect the ends of the two opposing 90° arc segments of the container.

2. The method of claim 1, wherein any particles in the container are pre-positioned in the heel of the container by the steps of tilting the container and spinning, with the container being moved into a position within 5 to 15 degrees of the vertical for a trapezoidal pulse of rotational velocity whereby the particles are efficiently accelerated with uniform initial velocity within a shell region adjacent the inner walls of the container.

3. The method of claim 1, wherein substantially all particles within the container are detected and sized and wherein an inventory of particles within the container is calculated and obtained, and whereby said inventory is used to define rejectable particle-contained containers according to predetermined particle size and number criteria.

4. A method for the substantially complete detection of all particles, within a predetermined size range, contained in an injectable solution, in a transparent container therefore, having a circular cross section, said method comprising the steps of:

a) pre-positioning particles in the container whereby rotation of the container causes substantially all of the particles in the injectable solution in the container to rotate in a shell volume adjacent the inner walls of the container, with said shell volume having a predetermined thickness;

b) illuminating all the particles rotating within the shell volume with lighting means; and c) detecting with at least two photo detectors at least one of light scatter, light reflection and light extinguishing caused by said particles, with the photo detector means having a depth of focus of detection in which equally blurred images are viewed in opposite volumes of the container with respect to a plane through an axis of the container parallel to a plane through the photo detector means;

characterized in that the photo detectors are positioned, relative to the container, whereby a focused imaging plane is formed at the container axis and then offset beyond the center of the cross section whereby the size of detected particles in the opposite volumes is accurately mathematically compensatible to an actual size; and wherein said lighting means provides a multiplicity of directed lights, with said container being masked relative to each of said lights whereby each light illuminates different volumes of the shell, with each volume being externally bounded by two opposing 90° arc segments of the container symmetrically disposed around principal optical planes passing through the respective center of the container and normal to the respective sensing faces of the photo detectors, and wherein the lighting means comprises at least two light sources, disposed at angles of 120° relative to each other and wherein at least two photo detectors sensors or two photo detectors sensor arrays are disposed orthogonally (90°) relative to each other.

5. The method of claim 4, wherein the inspection scan time for said illumination and detection is of a duration sufficient for between 5 to 10 scans of the container volume.

6. The method of claim 5, wherein focus of inspection lenses of the photo detectors is adjusted to obtain equal blur images in the shell volumes, at closest and furthest distances to the respective imaging lenses of the photo detectors.

7. The method of claim 6, wherein a depth of focus of each lens is adjusted to be equal to a predetermined container diameter, with each photo detector being moved to coincide with a focal plane that is not at the container center, to compensate for smaller focus depth in the portion of the shell volume closer to the imaging means.

8. The method of claim 7, wherein two orthogonal detectors are positioned around a plane perpendicularly passing through an axis of the container.

9. The method of claim 7, wherein with the particle illumination detection by each of the photo detectors, separate formulas for size determination of particle blur images are utilized to compensate for particle position in either the closest and furthest portions of the shell volumes, during detection, with a size differential blur image, to thereby provide equalization of particle sizes.

10. The method of claim 9, wherein determination of whether particles are contained in the closest or furthest portions of the opposite volumes, for applying said formulas, is effected by determining the sequence of movement of individual particles, with front and rear positioned particles moving in opposite directions.

11. The method of claim 10, wherein the position of the particle within the 90° arc but offset from the detector axis by the imaging distance are determined by sine-cosine functions in conjunction with particle movement, wherein a position obtained is used to correlate actual blur particle size detection to a corrected size.

12. The method of claim 10, wherein the light source is provided with intensity stabilization means which samples an average light intensity produced by the light source to provide pixel by pixel normalization of the intensity of the image light flux with the light intensity at each pixel being compared to the light intensity of a neighboring pixel.

13. The method of claim 12, wherein the intensity stabilization means comprises a feedback loop.

* * * * *